(12) United States Patent
Stotz et al.

(10) Patent No.: US 12,222,267 B2
(45) Date of Patent: Feb. 11, 2025

(54) ANALYSIS DEVICE AND METHOD FOR ANALYZING A VISCOSITY OF A FLUID

(71) Applicant: KARDION GMBH, Stuttgart (DE)

(72) Inventors: Ingo Stotz, Ditzingen (DE); Thomas Alexander Schlebusch, Renningen (DE); Tobias Schmid, Stuttgart (DE)

(73) Assignee: KARDION GMBH, Stuttgart (DE)

( * ) Notice: Subject to any disclaimer, the term of this patent is extended or adjusted under 35 U.S.C. 154(b) by 946 days.

(21) Appl. No.: 15/734,489

(22) PCT Filed: Jun. 6, 2019

(86) PCT No.: PCT/EP2019/064810
§ 371 (c)(1),
(2) Date: Jul. 20, 2021

(87) PCT Pub. No.: WO2019/234169
PCT Pub. Date: Dec. 12, 2019

(65) Prior Publication Data
US 2022/0050037 A1 Feb. 17, 2022

(30) Foreign Application Priority Data
Jun. 6, 2018 (DE) .......................... 102018208945.0

(51) Int. Cl.
*G01N 11/04* (2006.01)
*A61M 60/174* (2021.01)
(Continued)

(52) U.S. Cl.
CPC ........... *G01N 11/04* (2013.01); *A61M 60/174* (2021.01); *A61M 60/216* (2021.01);
(Continued)

(58) Field of Classification Search
CPC ............................ A61M 60/422; G01N 11/04
(Continued)

(56) References Cited

U.S. PATENT DOCUMENTS 3,088,323 A 5/1963 Welkowitz et al.
4,023,562 A 5/1977 Hynecek et al.
(Continued)

FOREIGN PATENT DOCUMENTS

| CA | 3 122 415 | 7/2020 |
| CN | 1192351 A | 9/1998 |

(Continued)

OTHER PUBLICATIONS

Hertz Ph.D. et al, "Ultrasonic Engineering in Heart Diagnosis", The American Journal of Cardiology, Jan. 1967, vol. 19, No. 1, pp. 6-17.
(Continued)

*Primary Examiner* — Nadia A Mahmood
(74) *Attorney, Agent, or Firm* — Knobbe, Martens, Olson & Bear, LLP

(57) ABSTRACT

The approach presented here relates to an analysis device (100) for analyzing a viscosity of a fluid (217). The analysis device (100) comprises a detection device (110) and a provisioning device (115). The detection device (110) is formed to determine the viscosity of the fluid (217) using at least one Doppler parameter of a Doppler spectrum of the fluid (217). The provisioning device (115) is formed to provide or transmit a viscosity signal that represents the viscosity determined by the detection device (110).

26 Claims, 6 Drawing Sheets

(51) Int. Cl.
*A61M 60/216* (2021.01)
*A61M 60/422* (2021.01)
*G01N 33/49* (2006.01)
*G01N 11/00* (2006.01)

(52) U.S. Cl.
CPC ........... *A61M 60/422* (2021.01); *G01N 33/49* (2013.01); *G01N 2011/0073* (2013.01)

(58) Field of Classification Search
USPC .......................................................... 606/16
See application file for complete search history.

(56) References Cited

U.S. PATENT DOCUMENTS

| | | | |
|---|---|---|---|
| 4,559,952 A | 12/1985 | Angelsen et al. |
| 4,781,525 A | 11/1988 | Hubbard et al. |
| 4,888,011 A | 12/1989 | Kung et al. |
| 4,889,131 A | 12/1989 | Salem et al. |
| 4,902,272 A | 2/1990 | Milder et al. |
| 5,045,051 A | 9/1991 | Milder et al. |
| 5,269,811 A | 12/1993 | Hayes |
| 5,289,821 A | 3/1994 | Swartz |
| 5,456,715 A | 10/1995 | Liotta |
| 5,527,159 A | 6/1996 | Bozeman, Jr. et al. |
| 5,581,038 A | 12/1996 | Lampropoulos |
| 5,613,935 A | 3/1997 | Jarvik |
| 5,662,115 A | 9/1997 | Torp |
| 5,676,651 A | 10/1997 | Larson, Jr. et al. |
| 5,720,771 A | 2/1998 | Snell |
| 5,752,976 A | 5/1998 | Duffin et al. |
| 5,766,207 A | 6/1998 | Potter et al. |
| 5,827,203 A | 10/1998 | Nita |
| 5,865,759 A | 2/1999 | Koblanski |
| 5,888,242 A | 3/1999 | Antaki et al. |
| 5,904,708 A | 5/1999 | Goedeke |
| 5,911,685 A | 6/1999 | Siess et al. |
| 5,964,694 A | 10/1999 | Siess et al. |
| 5,980,465 A | 11/1999 | Elgas |
| 6,007,478 A | 12/1999 | Siess et al. |
| 6,024,704 A | 2/2000 | Meador et al. |
| 6,053,873 A | 4/2000 | Govari et al. |
| 6,176,822 B1 | 1/2001 | Nix et al. |
| 6,183,412 B1 | 2/2001 | Benkowsi et al. |
| 6,185,460 B1 | 2/2001 | Thompson |
| 6,190,324 B1 | 2/2001 | Kieval et al. |
| 6,210,318 B1 | 4/2001 | Lederman |
| 6,231,498 B1 | 5/2001 | Pfeiffer et al. |
| 6,245,007 B1 | 6/2001 | Bedingham et al. |
| 6,314,322 B1 | 11/2001 | Rosenberg |
| 6,351,048 B1 | 2/2002 | Schob et al. |
| 6,398,734 B1 | 6/2002 | Cimochowski et al. |
| 6,432,136 B1 | 8/2002 | Weiss et al. |
| 6,438,409 B1 | 8/2002 | Malik et al. |
| 6,512,949 B1 | 1/2003 | Combs et al. |
| 6,530,876 B1 | 3/2003 | Spence |
| 6,540,658 B1 | 4/2003 | Fasciano et al. |
| 6,540,659 B1 | 4/2003 | Milbocker |
| 6,561,975 B1 | 5/2003 | Pool et al. |
| 6,579,257 B1 | 6/2003 | Elgas et al. |
| 6,602,182 B1 | 8/2003 | Milbocker |
| 6,605,032 B2 | 8/2003 | Benkowsi et al. |
| 6,652,447 B2 | 11/2003 | Benkowsi et al. |
| 6,731,976 B2 | 5/2004 | Penn et al. |
| 6,879,126 B2 | 4/2005 | Paden et al. |
| 6,912,423 B2 | 6/2005 | Ley et al. |
| 6,949,066 B2 | 9/2005 | Bearnson et al. |
| 6,984,201 B2 | 1/2006 | Khaghani et al. |
| 7,010,954 B2 | 3/2006 | Siess |
| 7,022,100 B1 | 4/2006 | Aboul-Hosn et al. |
| 7,024,244 B2 | 4/2006 | Muhlenberg et al. |
| 7,070,555 B2 | 7/2006 | Siess |
| 7,083,588 B1 | 8/2006 | Shmulewitz et al. |
| 7,138,776 B1 | 11/2006 | Gauthier et al. |
| 7,160,243 B2 | 1/2007 | Medvedev |
| 7,175,588 B2 | 2/2007 | Morello |
| 7,177,681 B2 | 2/2007 | Xhu |
| 7,238,151 B2 | 7/2007 | Frazier |
| 7,396,327 B2 | 7/2008 | Morello |
| 7,513,864 B2 | 4/2009 | Kantrowitz et al. |
| 7,520,850 B2 | 4/2009 | Brockway |
| 7,527,599 B2 | 5/2009 | Hickey |
| 7,591,777 B2 | 9/2009 | LaRose |
| 7,744,560 B2 | 6/2010 | Struble |
| 7,794,384 B2 | 9/2010 | Sugiura et al. |
| 7,819,916 B2 | 10/2010 | Yaegashi |
| 7,850,593 B2 | 12/2010 | Vincent et al. |
| 7,850,594 B2 | 12/2010 | Sutton et al. |
| 7,856,335 B2 | 12/2010 | Morello et al. |
| 7,862,501 B2 | 1/2011 | Woodward et al. |
| 7,951,062 B2 | 5/2011 | Morello |
| 7,951,129 B2 | 5/2011 | Chinchoy |
| 7,963,905 B2 | 6/2011 | Salmonsen et al. |
| 7,988,728 B2 | 8/2011 | Ayre |
| 8,075,472 B2 | 12/2011 | Zilbershlag et al. |
| 8,190,390 B2 | 5/2012 | Morello et al. |
| 8,211,028 B2 | 7/2012 | Karamanoglu et al. |
| 8,303,482 B2 | 11/2012 | Schima et al. |
| 8,323,173 B2 | 12/2012 | Benkowsi et al. |
| 8,435,182 B1 | 5/2013 | Tamura |
| 8,449,444 B2 | 5/2013 | Poirier |
| 8,545,380 B2 | 10/2013 | Farnan et al. |
| 8,585,572 B2 | 11/2013 | Mehmanesh |
| 8,591,393 B2 | 11/2013 | Walters et al. |
| 8,594,790 B2 | 11/2013 | Kjellstrom et al. |
| 8,622,949 B2 | 1/2014 | Zafirelis et al. |
| 8,657,733 B2 | 2/2014 | Ayre et al. |
| 8,657,875 B2 | 2/2014 | Kung et al. |
| 8,715,151 B2 | 5/2014 | Poirier |
| 8,747,293 B2 | 6/2014 | Arndt et al. |
| 8,849,398 B2 | 9/2014 | Evans |
| 8,864,643 B2 | 10/2014 | Reichenbach et al. |
| 8,864,644 B2 | 10/2014 | Yomtov |
| 8,876,685 B2 | 11/2014 | Crosby et al. |
| 8,882,477 B2 | 11/2014 | Fritz, IV et al. |
| 8,888,728 B2 | 11/2014 | Aboul-Hosn et al. |
| 8,897,873 B2 | 11/2014 | Schima et al. |
| 8,903,492 B2 | 12/2014 | Soykan et al. |
| 9,091,271 B2 | 7/2015 | Bourque |
| 9,297,735 B2 | 3/2016 | Graichen et al. |
| 9,308,305 B2 | 4/2016 | Chen et al. |
| 9,345,824 B2 | 5/2016 | Mohl et al. |
| 9,371,826 B2 | 6/2016 | Yanai et al. |
| 9,427,508 B2 | 8/2016 | Reyes et al. |
| 9,474,840 B2 | 10/2016 | Siess |
| 9,492,601 B2 | 11/2016 | Casas et al. |
| 9,511,179 B2 | 12/2016 | Casas et al. |
| 9,555,173 B2 | 1/2017 | Spanier |
| 9,555,175 B2 | 1/2017 | Bulent et al. |
| 9,556,873 B2 | 1/2017 | Yanai et al. |
| 9,566,374 B2 | 2/2017 | Spence et al. |
| 9,636,442 B2 | 5/2017 | Karmon et al. |
| 9,656,010 B2 | 5/2017 | Burke |
| 9,669,142 B2 | 6/2017 | Spanier et al. |
| 9,669,144 B2 | 6/2017 | Spanier et al. |
| 9,694,123 B2 | 7/2017 | Bourque et al. |
| 9,713,701 B2 | 7/2017 | Sarkar et al. |
| 9,744,282 B2 | 8/2017 | Rosenberg et al. |
| 9,789,236 B2 | 10/2017 | Bonde |
| 9,833,550 B2 | 12/2017 | Siess |
| 9,848,899 B2 | 12/2017 | Sliwa et al. |
| 9,849,224 B2 | 12/2017 | Angwin et al. |
| 9,878,087 B2 | 1/2018 | Richardson et al. |
| 9,943,236 B2 | 4/2018 | Bennett et al. |
| 9,950,102 B2 | 4/2018 | Spence et al. |
| 9,974,894 B2 | 5/2018 | Morello |
| 9,999,714 B2 | 6/2018 | Spanier et al. |
| 10,010,662 B2 | 7/2018 | Wiesener et al. |
| 10,022,480 B2 | 7/2018 | Greatrex et al. |
| 10,029,037 B2 | 7/2018 | Muller et al. |
| 10,052,420 B2 | 8/2018 | Medvedev et al. |
| 10,279,093 B2 | 5/2019 | Reichenbach et al. |
| 10,322,217 B2 | 6/2019 | Spence |
| 10,342,906 B2 | 7/2019 | D'Ambrosio et al. |

(56) References Cited

U.S. PATENT DOCUMENTS

| | | |
|---|---|---|
| 10,350,342 B2 | 7/2019 | Thomas et al. |
| 10,357,598 B2 | 7/2019 | Aboul-Hosn et al. |
| 10,376,162 B2 | 8/2019 | Edelman et al. |
| 10,413,651 B2 | 9/2019 | Yomtov et al. |
| 10,426,879 B2 | 10/2019 | Farnan |
| 10,449,275 B2 | 10/2019 | Corbett |
| 10,500,322 B2 | 12/2019 | Karch |
| 10,525,178 B2 | 1/2020 | Zeng |
| 10,549,020 B2 | 2/2020 | Spence et al. |
| 10,561,771 B2 | 2/2020 | Heilman et al. |
| 10,561,772 B2 | 2/2020 | Schumacher |
| 10,561,773 B2 | 2/2020 | Ferrari et al. |
| 10,632,241 B2 | 4/2020 | Schenck et al. |
| 10,660,998 B2 | 5/2020 | Hodges |
| 10,668,195 B2 | 6/2020 | Flores |
| 10,732,583 B2 | 8/2020 | Rudser |
| 10,857,275 B2 | 12/2020 | Granegger |
| 10,864,308 B2 | 12/2020 | Muller et al. |
| 11,027,114 B2 | 6/2021 | D'Ambrosio et al. |
| RE48,649 E | 7/2021 | Siess |
| 11,067,085 B2 | 7/2021 | Granegger et al. |
| 11,120,908 B2 | 9/2021 | Agnello et al. |
| 11,131,968 B2 | 9/2021 | Rudser |
| 11,147,960 B2 | 10/2021 | Spanier et al. |
| 11,154,701 B2 | 10/2021 | Reyes et al. |
| 11,154,702 B2 | 10/2021 | Kadrolkar et al. |
| 11,185,682 B2 | 11/2021 | Farnan |
| 11,191,945 B2 | 12/2021 | Siess et al. |
| 11,197,618 B2 | 12/2021 | Edelman et al. |
| 11,217,344 B2 | 1/2022 | Agnello |
| 11,235,139 B2 | 2/2022 | Kudlik |
| 11,241,572 B2 | 2/2022 | Dague et al. |
| 11,273,299 B2 | 3/2022 | Wolman et al. |
| 11,285,310 B2 | 3/2022 | Curran et al. |
| 11,285,311 B2 | 3/2022 | Siess et al. |
| 11,298,524 B2 | 4/2022 | El Katerji et al. |
| 11,311,711 B2 | 4/2022 | Casas et al. |
| 11,316,679 B2 | 4/2022 | Agnello |
| 11,320,382 B2 | 5/2022 | Aikawa |
| 11,324,395 B2 | 5/2022 | Banik et al. |
| 11,331,082 B2 | 5/2022 | Itoh et al. |
| 11,337,724 B2 | 5/2022 | Masubuchi et al. |
| 11,338,125 B2 | 5/2022 | Liu et al. |
| 11,351,356 B2 | 6/2022 | Mohl |
| 11,351,357 B2 | 6/2022 | Mohl |
| 11,351,358 B2 | 6/2022 | Nix et al. |
| 11,357,438 B2 | 6/2022 | Stewart et al. |
| 11,357,968 B2 | 6/2022 | El Katerji et al. |
| 11,376,415 B2 | 7/2022 | Mohl |
| 11,376,419 B2 | 7/2022 | Reyes et al. |
| 11,389,639 B2 | 7/2022 | Casas |
| 11,389,641 B2 | 7/2022 | Nguyen et al. |
| 11,413,444 B2 | 8/2022 | Nix et al. |
| 11,413,445 B2 | 8/2022 | Brown et al. |
| 11,420,041 B2 | 8/2022 | Karch |
| 11,439,806 B2 | 9/2022 | Kimball et al. |
| 11,446,481 B2 | 9/2022 | Wolman et al. |
| 11,478,629 B2 | 10/2022 | Harjes et al. |
| 11,517,740 B2 | 12/2022 | Agarwa et al. |
| 11,521,723 B2 | 12/2022 | Liu et al. |
| 11,524,165 B2 | 12/2022 | Tan et al. |
| 11,527,322 B2 | 12/2022 | Agnello et al. |
| 11,529,062 B2 | 12/2022 | Moyer et al. |
| 11,554,260 B2 | 1/2023 | Reyes et al. |
| 11,572,879 B2 | 2/2023 | Mohl |
| 11,574,741 B2 | 2/2023 | Tan et al. |
| 11,577,068 B2 | 2/2023 | Spence et al. |
| 11,581,083 B2 | 2/2023 | El Katerji et al. |
| 11,583,659 B2 | 2/2023 | Pfeffer et al. |
| 11,587,337 B2 | 2/2023 | Lemay et al. |
| 11,590,337 B2 | 2/2023 | Granegger et al. |
| 11,622,695 B1 | 4/2023 | Adriola et al. |
| 11,628,293 B2 | 4/2023 | Gandhi et al. |
| 11,639,722 B2 | 5/2023 | Medvedev et al. |
| 11,648,386 B2 | 5/2023 | Poirer |
| 11,653,841 B2 | 5/2023 | Reyes et al. |
| 11,666,746 B2 | 6/2023 | Ferrari et al. |
| 11,668,321 B2 | 6/2023 | Richert et al. |
| 11,674,517 B2 | 6/2023 | Mohl |
| 11,676,718 B2 | 6/2023 | Agnello et al. |
| 11,684,276 B2 | 6/2023 | Cros et al. |
| 11,684,769 B2 | 6/2023 | Harjes et al. |
| 11,694,539 B2 | 7/2023 | Kudlik et al. |
| 11,694,813 B2 | 7/2023 | El Katerji et al. |
| 11,696,782 B2 | 7/2023 | Carlson et al. |
| 11,707,617 B2 | 7/2023 | Reyes et al. |
| 11,712,167 B2 | 8/2023 | Medvedev et al. |
| 11,754,077 B1 | 9/2023 | Mohl |
| D1,001,145 S | 10/2023 | Lussier et al. |
| D1,001,146 S | 10/2023 | Lussier et al. |
| 11,771,885 B2 | 10/2023 | Liu et al. |
| 11,779,234 B2 | 10/2023 | Harjes et al. |
| 11,781,551 B2 | 10/2023 | Yanai et al. |
| 11,790,487 B2 | 10/2023 | Barbato et al. |
| 11,793,994 B2 | 10/2023 | Josephy et al. |
| 11,806,116 B2 | 11/2023 | Tuval et al. |
| 11,806,517 B2 | 11/2023 | Petersen |
| 11,806,518 B2 | 11/2023 | Michelena et al. |
| 11,813,079 B2 | 11/2023 | Lau et al. |
| 11,818,782 B2 | 11/2023 | Doudian et al. |
| 11,824,381 B2 | 11/2023 | Conyers et al. |
| 11,826,127 B2 | 11/2023 | Casas |
| 11,832,793 B2 | 12/2023 | McWeeney et al. |
| 11,832,868 B2 | 12/2023 | Smail et al. |
| 11,837,364 B2 | 12/2023 | Lee et al. |
| 11,844,592 B2 | 12/2023 | Tuval et al. |
| 11,844,940 B2 | 12/2023 | D'Ambrosio et al. |
| 11,850,073 B2 | 12/2023 | Wright et al. |
| 11,850,414 B2 | 12/2023 | Schenck et al. |
| 11,850,415 B2 | 12/2023 | Schwammenthal et al. |
| D1,012,284 S | 1/2024 | Glaser et al. |
| 11,857,345 B2 | 1/2024 | Hanson et al. |
| 11,864,878 B2 | 1/2024 | Duval et al. |
| 11,872,384 B2 | 1/2024 | Cotter |
| 11,883,207 B2 | 1/2024 | El Katerji et al. |
| D1,014,552 S | 2/2024 | Lussier et al. |
| 11,890,082 B2 | 2/2024 | Cros et al. |
| 11,896,199 B2 | 2/2024 | Lent et al. |
| 11,900,660 B2 | 2/2024 | Saito et al. |
| 11,903,657 B2 | 2/2024 | Geric et al. |
| 11,906,411 B2 | 2/2024 | Graichen et al. |
| 11,911,550 B2 | 2/2024 | Itamochi et al. |
| D1,017,634 S | 3/2024 | Lussier et al. |
| D1,017,699 S | 3/2024 | Moore et al. |
| 11,923,078 B2 | 3/2024 | Fallen et al. |
| 11,923,093 B2 | 3/2024 | Moffitt et al. |
| 11,925,794 B2 | 3/2024 | Malkin et al. |
| 11,931,073 B2 | 3/2024 | Walsh et al. |
| 11,931,528 B2 | 3/2024 | Rohl et al. |
| 11,931,588 B2 | 3/2024 | Aghassian |
| 11,986,274 B2 | 5/2024 | Edelman |
| 12,017,076 B2 | 6/2024 | Tan et al. |
| 12,023,476 B2 | 7/2024 | Tuval et al. |
| 12,029,891 B2 | 7/2024 | Siess et al. |
| 12,059,559 B2 | 8/2024 | Muller et al. |
| 12,076,544 B2 | 9/2024 | Siess et al. |
| 2001/0016686 A1 | 8/2001 | Okada et al. |
| 2001/0037093 A1 | 11/2001 | Benkowski et al. |
| 2001/0039828 A1 | 11/2001 | Shin et al. |
| 2002/0022785 A1 | 2/2002 | Romano |
| 2002/0147495 A1 | 10/2002 | Petroff |
| 2002/0151761 A1* | 10/2002 | Viole .................. A61M 60/152 600/16 |
| 2003/0069465 A1 | 4/2003 | Benkowski et al. |
| 2003/0130581 A1 | 7/2003 | Salo et al. |
| 2003/0139643 A1 | 7/2003 | Smith et al. |
| 2003/0167002 A1 | 9/2003 | Nagar et al. |
| 2003/0191357 A1 | 10/2003 | Frazier |
| 2004/0022640 A1 | 2/2004 | Siess et al. |
| 2004/0044266 A1 | 3/2004 | Siess et al. |
| 2004/0065143 A1 | 4/2004 | Husher |
| 2004/0130009 A1 | 7/2004 | Tangpuz |
| 2004/0167376 A1 | 8/2004 | Peters et al. |
| 2004/0167410 A1 | 8/2004 | Hettrick |

(56) References Cited

U.S. PATENT DOCUMENTS

| | | |
|---|---|---|
| 2004/0225177 A1 | 11/2004 | Coleman et al. |
| 2004/0241019 A1 | 12/2004 | Goldowsky |
| 2004/0260346 A1 | 12/2004 | Overall et al. |
| 2005/0001324 A1 | 1/2005 | Dunn |
| 2005/0019167 A1 | 1/2005 | Nusser et al. |
| 2005/0107658 A1 | 5/2005 | Brockway |
| 2005/0126268 A1 | 6/2005 | Ouriev et al. |
| 2005/0267322 A1 | 12/2005 | LaRose |
| 2006/0030809 A1 | 2/2006 | Barzilay et al. |
| 2006/0108697 A1 | 5/2006 | Wang |
| 2006/0108901 A1 | 5/2006 | Mao-Chin |
| 2006/0122583 A1 | 6/2006 | Pesach et al. |
| 2006/0196277 A1 | 9/2006 | Allen et al. |
| 2006/0229488 A1 | 10/2006 | Ayre et al. |
| 2006/0287600 A1 | 12/2006 | McEowen |
| 2006/0287604 A1 | 12/2006 | Hickey |
| 2007/0060787 A1 | 3/2007 | Peters et al. |
| 2007/0073352 A1 | 3/2007 | Euler et al. |
| 2007/0088214 A1 | 4/2007 | Shuros et al. |
| 2007/0156006 A1 | 7/2007 | Smith et al. |
| 2007/0255352 A1 | 11/2007 | Roline et al. |
| 2007/0266778 A1 | 11/2007 | Corey et al. |
| 2007/0282209 A1 | 12/2007 | Lui et al. |
| 2007/0299325 A1 | 12/2007 | Farrell et al. |
| 2008/0015517 A1 | 1/2008 | Geistert et al. |
| 2008/0082005 A1 | 4/2008 | Stern et al. |
| 2008/0091239 A1 | 4/2008 | Johansson et al. |
| 2008/0097595 A1 | 4/2008 | Gabbay |
| 2008/0102096 A1 | 5/2008 | Molin et al. |
| 2008/0108901 A1 | 5/2008 | Baba et al. |
| 2008/0108930 A1 | 5/2008 | Weitzel et al. |
| 2008/0133006 A1 | 6/2008 | Crosby et al. |
| 2008/0146996 A1 | 6/2008 | Smisson |
| 2008/0210016 A1 | 9/2008 | Zwirn et al. |
| 2008/0262289 A1 | 10/2008 | Goldowsky |
| 2008/0262361 A1 | 10/2008 | Gutfinger et al. |
| 2008/0269822 A1 | 10/2008 | Ljungstrom et al. |
| 2008/0275339 A1 | 11/2008 | Thiemann et al. |
| 2008/0306328 A1 | 12/2008 | Ercolani |
| 2009/0024042 A1 | 1/2009 | Nunez et al. |
| 2009/0025459 A1 | 1/2009 | Zhang et al. |
| 2009/0064755 A1 | 3/2009 | Fleischli et al. |
| 2009/0105799 A1 | 4/2009 | Hekmat et al. |
| 2009/0131765 A1 | 5/2009 | Roschak et al. |
| 2009/0204163 A1 | 8/2009 | Shuros et al. |
| 2009/0226328 A1 | 9/2009 | Morello |
| 2009/0312650 A1 | 12/2009 | Maile et al. |
| 2010/0010354 A1 | 1/2010 | Skerl et al. |
| 2010/0082099 A1 | 4/2010 | Vodermayer et al. |
| 2010/0087742 A1 | 4/2010 | Bishop et al. |
| 2010/0160801 A1 | 6/2010 | Takatani et al. |
| 2010/0219967 A1 | 9/2010 | Kaufmann |
| 2010/0222632 A1 | 9/2010 | Poirier |
| 2010/0222633 A1 | 9/2010 | Poirier |
| 2010/0222635 A1 | 9/2010 | Poirier |
| 2010/0222878 A1 | 9/2010 | Poirier |
| 2010/0268017 A1 | 10/2010 | Siess |
| 2010/0298625 A1 | 11/2010 | Reichenbach et al. |
| 2010/0324378 A1 | 12/2010 | Tran et al. |
| 2011/0004075 A1 | 1/2011 | Stahmann et al. |
| 2011/0022057 A1 | 1/2011 | Eigler et al. |
| 2011/0071336 A1 | 3/2011 | Yomtov |
| 2011/0144744 A1 | 6/2011 | Wampler |
| 2011/0184301 A1 | 7/2011 | Holmstrom |
| 2011/0218435 A1 | 9/2011 | Srinivasan et al. |
| 2011/0230068 A1 | 9/2011 | Pahl |
| 2012/0022645 A1 | 1/2012 | Burke |
| 2012/0084024 A1 | 4/2012 | Norcross, Jr. |
| 2012/0150089 A1 | 6/2012 | Penka et al. |
| 2012/0203476 A1 | 8/2012 | Dam |
| 2012/0247200 A1 | 10/2012 | Ahonen et al. |
| 2012/0310037 A1 | 12/2012 | Choi et al. |
| 2012/0330214 A1 | 12/2012 | Peters et al. |
| 2013/0041204 A1 | 2/2013 | Heilman et al. |
| 2013/0046129 A1 | 2/2013 | Medvedev et al. |
| 2013/0066141 A1 | 3/2013 | Doerr et al. |
| 2013/0066142 A1 | 3/2013 | Doerr et al. |
| 2013/0072846 A1 | 3/2013 | Heide et al. |
| 2013/0116575 A1 | 5/2013 | Mickle et al. |
| 2013/0144379 A1 | 6/2013 | Najafi et al. |
| 2013/0289376 A1 | 10/2013 | Lang |
| 2013/0303831 A1 | 11/2013 | Evans |
| 2014/0005467 A1 | 1/2014 | Farnan et al. |
| 2014/0013852 A1 | 1/2014 | Brown et al. |
| 2014/0100414 A1 | 4/2014 | Tamez et al. |
| 2014/0114202 A1 | 4/2014 | Hein et al. |
| 2014/0128659 A1 | 5/2014 | Heuring et al. |
| 2014/0200389 A1 | 7/2014 | Yanai et al. |
| 2014/0243688 A1 | 8/2014 | Caron et al. |
| 2014/0275720 A1 | 9/2014 | Ferrari |
| 2014/0296677 A1 | 10/2014 | McEowen |
| 2014/0303426 A1 | 10/2014 | Kerkhoffs et al. |
| 2014/0342203 A1 | 11/2014 | Elian |
| 2015/0032007 A1 | 1/2015 | Ottevanger et al. |
| 2015/0141832 A1 | 5/2015 | Yu et al. |
| 2015/0141842 A1 | 5/2015 | Spanier et al. |
| 2015/0157216 A1 | 6/2015 | Stigall et al. |
| 2015/0174307 A1 | 6/2015 | Eckman et al. |
| 2015/0190092 A1 | 7/2015 | Mori |
| 2015/0250935 A1 | 9/2015 | Anderson et al. |
| 2015/0273184 A1 | 10/2015 | Scott et al. |
| 2015/0290372 A1 | 10/2015 | Muller et al. |
| 2015/0306290 A1 | 10/2015 | Rosenberg et al. |
| 2015/0306291 A1 | 10/2015 | Bonde et al. |
| 2015/0307344 A1 | 10/2015 | Ernst |
| 2015/0327921 A1 | 11/2015 | Govari |
| 2015/0335804 A1 | 11/2015 | Marseille et al. |
| 2015/0365738 A1 | 12/2015 | Purvis et al. |
| 2016/0000983 A1 | 1/2016 | Mohl et al. |
| 2016/0008531 A1 | 1/2016 | Wang et al. |
| 2016/0022889 A1 | 1/2016 | Bluvshtein et al. |
| 2016/0022890 A1 | 1/2016 | Schwammenthal et al. |
| 2016/0045165 A1 | 2/2016 | Braido et al. |
| 2016/0095968 A1 | 4/2016 | Rudser |
| 2016/0101230 A1 | 4/2016 | Ochsner et al. |
| 2016/0144166 A1 | 5/2016 | Decré et al. |
| 2016/0151553 A1 | 6/2016 | Bonde |
| 2016/0166747 A1 | 6/2016 | Frazier et al. |
| 2016/0213828 A1 | 7/2016 | Sievers |
| 2016/0250399 A1 | 9/2016 | Tiller et al. |
| 2016/0278856 A1 | 9/2016 | Panescu |
| 2016/0302672 A1 | 10/2016 | Kuri |
| 2016/0317043 A1 | 11/2016 | Campo |
| 2016/0338629 A1 | 11/2016 | Doerr |
| 2017/0010144 A1 | 1/2017 | Lenner et al. |
| 2017/0021070 A1 | 1/2017 | Petersen |
| 2017/0049945 A1 | 2/2017 | Halvorsen et al. |
| 2017/0086780 A1 | 3/2017 | Sokulin et al. |
| 2017/0098491 A1 | 4/2017 | Ziaie et al. |
| 2017/0112985 A1 | 4/2017 | Yomtov |
| 2017/0128646 A1 | 5/2017 | Karch |
| 2017/0136164 A1 | 5/2017 | Yeatts |
| 2017/0202575 A1 | 7/2017 | Stanfield et al. |
| 2017/0224279 A1 | 8/2017 | Cahan et al. |
| 2017/0239407 A1 | 8/2017 | Hayward |
| 2017/0258980 A1 | 9/2017 | Katsuki et al. |
| 2017/0348470 A1 | 12/2017 | D'Ambrosio et al. |
| 2017/0354812 A1 | 12/2017 | Callaghan et al. |
| 2018/0064860 A1 | 3/2018 | Nunez et al. |
| 2018/0078159 A1 | 3/2018 | Edelman et al. |
| 2018/0093070 A1 | 4/2018 | Cottone |
| 2018/0110910 A1 | 4/2018 | Rodemerk et al. |
| 2018/0199635 A1 | 7/2018 | Longinotti-Buitoni et al. |
| 2018/0250457 A1 | 9/2018 | Morello et al. |
| 2018/0256796 A1 | 9/2018 | Hansen |
| 2018/0256800 A1 | 9/2018 | Conyers et al. |
| 2018/0264182 A1 | 9/2018 | Spanier et al. |
| 2018/0280598 A1 | 10/2018 | Curran et al. |
| 2018/0316209 A1 | 11/2018 | Gliner |
| 2018/0326131 A1 | 11/2018 | Muller et al. |
| 2018/0353667 A1 | 12/2018 | Moyer et al. |
| 2018/0369469 A1 | 12/2018 | Le Duc De Lillers et al. |
| 2019/0001038 A1 | 1/2019 | Yomtov et al. |
| 2019/0054223 A1 | 2/2019 | Frazier et al. |

(56) References Cited

U.S. PATENT DOCUMENTS

| | | |
|---|---|---|
| 2019/0083690 A1 | 3/2019 | Siess et al. |
| 2019/0192752 A1 | 6/2019 | Tiller et al. |
| 2019/0192753 A1 | 6/2019 | Liu et al. |
| 2019/0209755 A1 | 7/2019 | Nix et al. |
| 2019/0209758 A1 | 7/2019 | Tuval et al. |
| 2019/0216995 A1 | 7/2019 | Kapur et al. |
| 2019/0217002 A1 | 7/2019 | Urakabe |
| 2019/0223877 A1 | 7/2019 | Nitzen et al. |
| 2019/0240680 A1 | 8/2019 | Hayakawa |
| 2019/0254543 A1 | 8/2019 | Hartholt et al. |
| 2019/0282741 A1 | 9/2019 | Franano et al. |
| 2019/0282744 A1 | 9/2019 | D'Ambrosio et al. |
| 2019/0351117 A1 | 11/2019 | Cambronne et al. |
| 2019/0351118 A1 | 11/2019 | Graichen et al. |
| 2020/0016309 A1 | 1/2020 | Kallenbach et al. |
| 2020/0038567 A1 | 2/2020 | Siess et al. |
| 2020/0060559 A1 | 2/2020 | Edelman et al. |
| 2020/0069857 A1 | 3/2020 | Schwammenthal et al. |
| 2020/0147283 A1 | 5/2020 | Tanner et al. |
| 2020/0164125 A1 | 5/2020 | Muller et al. |
| 2020/0164126 A1 | 5/2020 | Muller |
| 2020/0253583 A1 | 8/2020 | Brisken et al. |
| 2020/0312450 A1 | 10/2020 | Agnello et al. |
| 2021/0268264 A1 | 9/2021 | Stotz |
| 2021/0290087 A1 | 9/2021 | Schlebusch |
| 2021/0290930 A1 | 9/2021 | Kasel |
| 2021/0290933 A1 | 9/2021 | Stotz |
| 2021/0339002 A1 | 11/2021 | Schlebusch et al. |
| 2021/0339004 A1 | 11/2021 | Schlebusch et al. |
| 2021/0346674 A1 | 11/2021 | Baumbach et al. |
| 2021/0346675 A1 | 11/2021 | Schlebusch et al. |
| 2021/0346676 A1 | 11/2021 | Schlebusch et al. |
| 2021/0346677 A1 | 11/2021 | Baumbach et al. |
| 2021/0346678 A1 | 11/2021 | Baumbach et al. |
| 2021/0378523 A1 | 12/2021 | Budde |
| 2021/0379359 A1 | 12/2021 | Schellenberg |
| 2021/0379360 A1 | 12/2021 | Schellenberg |
| 2021/0393944 A1 | 12/2021 | Wenning |
| 2022/0016411 A1 | 1/2022 | Winterwerber |
| 2022/0032032 A1 | 2/2022 | Schlebusch et al. |
| 2022/0032036 A1 | 2/2022 | Baumbach et al. |
| 2022/0039669 A1 | 2/2022 | Schlebusch et al. |
| 2022/0047173 A1 | 2/2022 | Stotz et al. |
| 2022/0072298 A1 | 3/2022 | Spanier et al. |
| 2022/0076807 A1 | 3/2022 | Agnello |
| 2022/0079457 A1 | 3/2022 | Tuval et al. |
| 2022/0105339 A1 | 4/2022 | Nix et al. |
| 2022/0126085 A1 | 4/2022 | Farnan |
| 2022/0126086 A1 | 4/2022 | Schlebusch et al. |
| 2022/0142462 A1 | 5/2022 | Douk et al. |
| 2022/0161019 A1 | 5/2022 | Mitze et al. |
| 2022/0361762 A1 | 11/2022 | Lalancette |
| 2023/0173250 A1 | 6/2023 | Stigloher |
| 2023/0191141 A1 | 6/2023 | Wenning et al. |
| 2024/0011808 A1 | 1/2024 | Winzer et al. |
| 2024/0074828 A1 | 3/2024 | Wenning |
| 2024/0245902 A1 | 7/2024 | Schlebusch et al. |

FOREIGN PATENT DOCUMENTS

| | | |
|---|---|---|
| CN | 1222862 A | 7/1999 |
| CN | 1202871 C | 5/2005 |
| CN | 1661338 A | 8/2005 |
| CN | 101128168 | 2/2008 |
| CN | 101208045 | 6/2008 |
| CN | 101214158 | 7/2008 |
| CN | 101351237 | 1/2009 |
| CN | 101448535 | 6/2009 |
| CN | 101460094 | 6/2009 |
| CN | 101579233 | 11/2009 |
| CN | 201437016 | 4/2010 |
| CN | 101711683 | 5/2010 |
| CN | 201658687 | 12/2010 |
| CN | 102421372 | 4/2012 |
| CN | 102803923 | 11/2012 |
| CN | 103328018 | 9/2013 |
| CN | 103857326 | 6/2014 |
| CN | 103957957 | 7/2014 |
| CN | 104105449 | 10/2014 |
| CN | 104188687 | 12/2014 |
| CN | 106104229 | 11/2016 |
| CN | 106333707 | 1/2017 |
| CN | 206007680 | 3/2017 |
| CN | 107530479 | 1/2018 |
| CN | 107632167 | 1/2018 |
| CN | 109939282 | 6/2019 |
| CN | 209790495 | 12/2019 |
| CN | 210020563 | 2/2020 |
| DE | 195 20 920 | 12/1995 |
| DE | 198 21 307 | 10/1999 |
| DE | 100 59 714 | 5/2002 |
| DE | 100 60 275 | 6/2002 |
| DE | 101 44 269 | 3/2003 |
| DE | 102 26 305 | 10/2003 |
| DE | 10 2006 001 180 | 9/2007 |
| DE | 10 2009 007 216 | 8/2010 |
| DE | 10 2009 011 726 | 9/2010 |
| DE | 10 2009 025 464 | 1/2011 |
| DE | 10 2009 047 845 | 3/2011 |
| DE | 10 2011 106 142 | 12/2012 |
| DE | 20 2011 110 389 | 9/2013 |
| DE | 10 2015 004 177 | 10/2015 |
| DE | 10 2015 219 263 | 4/2017 |
| DE | 10 2015 222 199 | 5/2017 |
| DE | 20 2015 009 422 | 7/2017 |
| DE | 10 2012 207 042 | 9/2017 |
| DE | 10 2016 013 334 | 4/2018 |
| DE | 10 2018 208 536 | 12/2019 |
| DE | 10 2018 208 862 | 12/2019 |
| DE | 10 2018 208 916 | 12/2019 |
| DE | 10 2018 208 927 | 12/2019 |
| DE | 10 2018 208 945 | 12/2019 |
| DE | 10 2018 210 076 | 12/2019 |
| DE | 10 2018 212 153 | 1/2020 |
| DE | 10 2018 213 151 | 2/2020 |
| DE | 10 2018 213 350 | 2/2020 |
| DE | 10 2018 220 658 | 6/2020 |
| DE | 10 2018 222 505 | 6/2020 |
| DE | 10 2020 102 473 | 8/2021 |
| DE | 11 2020 003 151 | 3/2022 |
| EP | 0 794 411 | 9/1997 |
| EP | 0 916 359 | 5/1999 |
| EP | 1 062 959 | 12/2000 |
| EP | 1 339 443 | 11/2001 |
| EP | 1 011 803 | 9/2004 |
| EP | 1 354 606 | 6/2006 |
| EP | 2 143 385 | 1/2010 |
| EP | 2 175 770 | 4/2010 |
| EP | 2 187 807 | 6/2012 |
| EP | 2 570 143 | 3/2013 |
| EP | 2 401 003 | 10/2013 |
| EP | 1 871 441 | 11/2014 |
| EP | 2 859 911 | 4/2015 |
| EP | 2 213 227 | 8/2016 |
| EP | 2 835 141 | 8/2016 |
| EP | 3 088 016 | 11/2016 |
| EP | 2 585 129 | 3/2017 |
| EP | 2 945 661 | 11/2017 |
| EP | 2 136 861 | 12/2017 |
| EP | 3 020 426 | 12/2017 |
| EP | 3 287 154 | 2/2018 |
| EP | 3 205 359 | 8/2018 |
| EP | 3 205 360 | 8/2018 |
| EP | 3 389 738 | 8/2019 |
| EP | 2 505 090 | 12/2019 |
| EP | 3 668 560 | 6/2020 |
| EP | 3 720 520 | 10/2020 |
| EP | 3 753 594 | 12/2020 |
| EP | 3 357 523 | 1/2021 |
| EP | 3 490 628 | 2/2021 |
| EP | 3 487 548 | 3/2021 |
| EP | 3 509 661 | 3/2021 |
| EP | 3 515 523 | 3/2021 |
| EP | 3 528 863 | 3/2021 |

(56) References Cited

FOREIGN PATENT DOCUMENTS

| | | |
|---|---|---|
| EP | 3 615 103 | 3/2021 |
| EP | 4 271 461 | 3/2021 |
| EP | 3 131 600 | 6/2021 |
| EP | 3 131 615 | 6/2021 |
| EP | 3 463 505 | 9/2021 |
| EP | 3 884 970 | 9/2021 |
| EP | 2 599 510 | 10/2021 |
| EP | 3 003 421 | 10/2021 |
| EP | 3 027 241 | 10/2021 |
| EP | 3 668 561 | 10/2021 |
| EP | 3 164 168 | 12/2021 |
| EP | 3 344 129 | 12/2021 |
| EP | 3 624 867 | 3/2022 |
| EP | 3 651 822 | 3/2022 |
| EP | 3 689 389 | 3/2022 |
| EP | 3 737 436 | 3/2022 |
| EP | 3 984 589 | 4/2022 |
| EP | 3 654 006 | 5/2022 |
| EP | 3 737 310 | 7/2022 |
| EP | 2 999 400 | 8/2022 |
| EP | 3 711 788 | 8/2022 |
| EP | 3 694 573 | 9/2022 |
| EP | 3 600 477 | 10/2022 |
| EP | 3 897 768 | 10/2022 |
| EP | 2 892 583 | 1/2023 |
| EP | 3 370 797 | 1/2023 |
| EP | 3 597 231 | 1/2023 |
| EP | 3 668 562 | 1/2023 |
| EP | 3 856 275 | 1/2023 |
| EP | 3 003 420 | 2/2023 |
| EP | 3 397 299 | 2/2023 |
| EP | 3 046 594 | 3/2023 |
| EP | 3 938 005 | 4/2023 |
| EP | 3 685 562 | 5/2023 |
| EP | 3 397 298 | 7/2023 |
| EP | 3 809 959 | 7/2023 |
| EP | 2 072 150 | 9/2023 |
| EP | 2 961 984 | 9/2023 |
| EP | 3 352 808 | 9/2023 |
| EP | 3 768 156 | 9/2023 |
| EP | 4 052 754 | 10/2023 |
| EP | 3 157 596 | 11/2023 |
| EP | 3 766 428 | 11/2023 |
| EP | 3 781 027 | 11/2023 |
| EP | 4 061 470 | 11/2023 |
| EP | 4 070 720 | 11/2023 |
| EP | 3 449 958 | 12/2023 |
| EP | 3 687 596 | 12/2023 |
| EP | 3 768 340 | 12/2023 |
| EP | 3 801 675 | 1/2024 |
| EP | 3 566 636 | 2/2024 |
| EP | 3 634 526 | 2/2024 |
| EP | 3 768 347 | 2/2024 |
| EP | 3 790 606 | 2/2024 |
| EP | 3 930 780 | 2/2024 |
| EP | 3 397 147 | 3/2024 |
| EP | 3 782 695 | 3/2024 |
| EP | 3 854 448 | 3/2024 |
| EP | 4 140 532 | 5/2024 |
| EP | 3 693 038 | 6/2024 |
| EP | 3 970 765 | 7/2024 |
| EP | 3 854 444 | 9/2024 |
| ES | 2 913 485 | 6/2022 |
| JP | S59-080229 | 5/1984 |
| JP | S61-125329 | 6/1986 |
| JP | S62-113555 | 7/1987 |
| JP | S62-204733 | 9/1987 |
| JP | S62-282284 | 12/1987 |
| JP | S64-68236 | 3/1989 |
| JP | H02-055886 | 2/1990 |
| JP | H02-234750 | 9/1990 |
| JP | H05-079875 | 3/1993 |
| JP | H06-218044 | 8/1994 |
| JP | H07-047025 | 5/1995 |
| JP | H08-057042 | 3/1996 |
| JP | H08-066398 | 3/1996 |
| JP | H08-327527 | 12/1996 |
| JP | H10-052489 | 2/1998 |
| JP | H10-505766 | 6/1998 |
| JP | H11-239617 | 9/1999 |
| JP | 2000-512191 | 9/2000 |
| JP | 2001-037728 | 2/2001 |
| JP | 2001-506140 | 5/2001 |
| JP | 2001-276213 | 10/2001 |
| JP | 2002-525175 | 8/2002 |
| JP | 2003-019197 | 1/2003 |
| JP | 2003-047656 | 2/2003 |
| JP | 2003-062065 | 3/2003 |
| JP | 2004-515278 | 5/2004 |
| JP | 2005-028137 | 2/2005 |
| JP | 2005-192687 | 7/2005 |
| JP | 2006-528006 | 12/2006 |
| JP | 2007-222644 | 9/2007 |
| JP | 2008-511414 | 4/2008 |
| JP | 2006-518249 | 8/2008 |
| JP | 2008-178690 | 8/2008 |
| JP | 2009-504290 | 2/2009 |
| JP | 2009-240348 | 10/2009 |
| JP | 2010-518907 | 6/2010 |
| JP | 2012-520157 | 9/2012 |
| JP | 2013-128792 | 7/2013 |
| JP | 2014-524274 | 9/2014 |
| JP | 2015-514529 | 5/2015 |
| JP | 2015-514531 | 5/2015 |
| JP | 2015-515429 | 5/2015 |
| JP | 2015-122448 | 7/2015 |
| JP | 2015-527172 | 9/2015 |
| JP | 2015-181800 | 10/2015 |
| JP | 2016-002466 | 1/2016 |
| JP | 2016-509950 | 4/2016 |
| JP | 2017-500932 | 1/2017 |
| JP | 2017-176719 | 10/2017 |
| JP | 2017-532084 | 11/2017 |
| JP | 2019-523110 | 8/2019 |
| JP | 2020-072985 | 5/2020 |
| WO | WO 92/015239 | 9/1992 |
| WO | WO 98/043688 | 10/1998 |
| WO | WO 00/033047 | 6/2000 |
| WO | WO 2006/122001 | 11/2006 |
| WO | WO 2010/142286 | 12/2010 |
| WO | WO 2010/143272 | 12/2010 |
| WO | WO 2012/018917 | 2/2012 |
| WO | WO 2012/112378 | 8/2012 |
| WO | WO 2013/160443 | 10/2013 |
| WO | WO 2014/042925 | 3/2014 |
| WO | WO 2014/141284 | 9/2014 |
| WO | WO 2014/165635 | 10/2014 |
| WO | WO 2015/085220 | 6/2015 |
| WO | WO 2016/001284 | 1/2016 |
| WO | WO 2016/066180 | 5/2016 |
| WO | WO 2016/137743 | 9/2016 |
| WO | WO 2017/032751 | 3/2017 |
| WO | WO 2017/066257 | 4/2017 |
| WO | WO 2017/106190 | 6/2017 |
| WO | WO 2017/147291 | 8/2017 |
| WO | WO 2017/214118 | 12/2017 |
| WO | WO 2018/048800 | 3/2018 |
| WO | WO 2018/109038 | 6/2018 |
| WO | WO 2018/213089 | 11/2018 |
| WO | WO 2019/013794 | 1/2019 |
| WO | WO 2019/034670 | 2/2019 |
| WO | WO 2019/034775 | 2/2019 |
| WO | WO 2019/078723 | 4/2019 |
| WO | WO 2019/126721 | 6/2019 |
| WO | WO 2019/137911 | 7/2019 |
| WO | WO 2019/193604 | 10/2019 |
| WO | WO 2019/219883 | 11/2019 |
| WO | WO 2019/229210 | 12/2019 |
| WO | WO 2019/229220 | 12/2019 |
| WO | WO 2019/234145 | 12/2019 |
| WO | WO 2019/234146 | 12/2019 |
| WO | WO 2019/234148 | 12/2019 |
| WO | WO 2019/234149 | 12/2019 |
| WO | WO 2019/234151 | 12/2019 |

(56) References Cited

FOREIGN PATENT DOCUMENTS

| WO | WO 2019/234152 | 12/2019 |
| WO | WO 2019/234153 | 12/2019 |
| WO | WO 2019/234161 | 12/2019 |
| WO | WO 2019/234162 | 12/2019 |
| WO | WO 2019/234163 | 12/2019 |
| WO | WO 2019/234164 | 12/2019 |
| WO | WO 2019/234166 | 12/2019 |
| WO | WO 2019/234167 | 12/2019 |
| WO | WO 2019/234169 | 12/2019 |
| WO | WO 2019/243582 | 12/2019 |
| WO | WO 2020/030686 | 2/2020 |
| WO | WO 2020/030706 | 2/2020 |
| WO | WO 2020/064707 | 4/2020 |
| WO | WO 2020/089429 | 5/2020 |
| WO | WO 2020/198280 | 10/2020 |
| WO | WO 2020/243756 | 12/2020 |
| WO | WO 2022/074136 | 4/2022 |
| WO | WO 2022/109590 | 5/2022 |
| WO | WO 2022/173970 | 8/2022 |
| WO | WO 2023/049813 | 3/2023 |

OTHER PUBLICATIONS

International Search Report and Written Opinion received in PCT Application No. PCT/EP2019/064810, dated Aug. 1, 2019 in 15 pages.

International Preliminary Report on Patentability and Written Opinion received in PCT Application No. PCT/EP2019/064810, dated Aug. 18, 2020 in 20 pages.

Kong et al., "A Stein Equation Approach for Solutions to the Diophantine Equations," 2010 Chinese Control and Decision Conference, Xuzhou, May 26, 2010, pp. 3024-3028.

Koseli et al., "Online Viscosity Measurement of Complex Solutions Using Ultrasound Doppler Velocimetry", Turk J Chem, Jan. 2006, vol. 30, pp. 297-305.

McCormick et al., "Resolution of a 2/spl pi/ Ambiguity Problem in Multiple Frequency Spectral Estimation," in IEEE Transactions on Aerospace and Electronic Systems, Jan. 1995, vol. 31, No. 1, pp. 2-8.

Syrmos et al., "A Generalized Bezout Equation in Output Feedback Design," Proceedings of the 31st IEEE Conference on Decision and Control, Tucson, AZ, USA, Dec. 1992, vol. 4, pp. 3590-3594.

Udesen et al., "A Simple Method to Reduce Aliasing Artifacts in Color Flow Mode Imaging", IEEE Ultrasonics Symposium, 2005, Rotterdam, The Netherlands, Sep. 18-21, 2005, pp. 1352-1355.

Lombardi et al., "Flow Rate Profiler: an instrument to measure blood velocity profiles", Ultrasonics, 2001, vol. 39, pp. 143-150.

Mushi et al., "Identification of Fluidic Element Models to Simulate the Short-Term Baroreflex", Proceedings of the 45th IEEE Conference on Decision & Control, San Diego, CA, Dec. 13-15, 2006, pp. 6.

Vollkron et al., "Advanced Suction Detection for an Axial Flow Pump", Artificial Organs, 2006, vol. 30, No. 9, pp. 665-670.

Vollkron et al., "Development of a Suction Detection System for Axial Blood Pumps", Artificial Organs, 2004, vol. 28, No. 8, pp. 709-716.

Atkinson et al., "Pulse-Doppler Ultrasound and Its Clinical Application", The Yale Journal of Biology and Medicine, 1977, vol. 50, pp. 367-373.

Leguy et al., "Assessment of Blood Volume Flow in Slightly Curved Arteries from a Single Velocity Profile", Journal of Biomechanics, 2009, pp. 1664-1672.

Sinha et al., "Effect of Mechanical Assistance of the Systemic Ventricle in Single Ventricle Circulation with Cavopulmonary Connection", The Journal of Thoracic and Cardiovascular Surgery, Apr. 2014, vol. 147, No. 4, pp. 1271-1275.

"Understanding Hot-Wire Anemometry", Advanced Thermal Solutions, Inc., 2007, pp. 13-17.

Vieli, A., "Doppler Flow Determination", BJA: British Journal of Anaesthesia, 1988, vol. 60, pp. 107S-112S.

Yuanyuan et al., "Characteristics Analysis for Doppler Ultrasound Blood Flow Signals", China Medical Device Information, 5(1), Feb. 28, 1999, pp. 36-42.

Zhang, Dabiao et al., "Design of Microwave Velocity and Distance Monitor System", Instrument Technique and Sensor, Hebei Normal University, Apr. 25, 2004, pp. 3.

Murali, Akila, "Design of Inductive Coils for Wireless Power Transfer to Pediatric Implants", A graduate project submitted in partial fulfillment of the requirements for the degree of Master of Science in Electrical Engineering, California State University, Northridge, May 2018, pp. 37.

* cited by examiner

ANALYSIS DEVICE AND METHOD FOR ANALYZING A VISCOSITY OF A FLUID

BACKGROUND

Field

The invention relates to an analysis device and a method for analyzing a viscosity of a fluid. The invention also relates to a computer program and a machine-readable storage medium on which the computer program is stored.

Description of the Related Art

PT (prothrombin time) and INR (International Normalized Ratio) are the standard measure for blood coagulation. Usually, the INR in blood samples is determined by adding thromboplastin and then measuring the time to coagulation. The determination can be carried out in the laboratory; meanwhile, test strip devices are now also available for self-measurement by the patient, comparable to the procedure of a blood sugar measurement. Coagulation management is essential for patients with cardiac assist systems to minimize pump thrombosis. Monitoring of blood viscosity as an INR substitute parameter may be sufficient for coagulation management.

EP 2175770 B1 describes an explicit blood viscosity sensor based on surface waves, abbreviated as SAW, for determining viscosity.

U.S. Pat. No. 7,591,777 B2 describes a viscosity determination in cardiac assist systems by the mechanical effect of the blood viscosity on the drive of the cardiac assist system.

SUMMARY

The task of the invention is to provide an improved method for analyzing a viscosity of a fluid and an improved analysis device for this purpose. In particular, it is a task of the invention to specify a method and a device that allows the viscosity of a fluid to be analyzed continuously and on a short time scale.

This task is achieved by the determination devices, systems, and methods disclosed herein. Advantageous embodiments of the invention are disclosed herein.

An analysis device for analyzing a viscosity of a fluid and a method according to the invention for analyzing a viscosity of a fluid and finally a corresponding computer program are presented below. Advantageous further embodiments and improvements of the subject matter specified herein are possible using the measures specified herein.

In light of this background, the approach presented here presents an analysis device for analyzing a viscosity of a fluid and a method for analyzing a viscosity of a fluid and finally a corresponding computer program according to the main claims. Advantageous further developments and improvements of the device specified in the independent claim are possible using the measures listed in the dependent claims.

The advantages achievable with the presented approach are that an analysis device presented here is designed to determine and provide or transmit the viscosity of a fluid quickly and easily using a real-time Doppler parameter of the fluid. A Doppler parameter can in this case be understood to mean a parameter that represents information about a change in a frequency of a signal emitted into the fluid to a frequency of a signal received from the fluid. For example, the Doppler parameter corresponds to a Doppler shift. In the present case, a Doppler spectrum can be understood to mean a spectrum that contains frequencies that result from a signal emitted into the fluid, as well as frequencies that result from a signal received from the fluid. This approach then can for example permit an analysis of the Doppler shift of different frequency components of signals emitted into the fluid with respect to the frequency components resulting from signals received from the fluid.

An analysis device for analyzing a viscosity of a fluid is presented. The analysis device comprises a detection device and a provisioning device. The detection device is formed to determine the viscosity of the fluid using at least one Doppler parameter of a Doppler spectrum of the fluid. The provisioning device is formed to provide or emit a viscosity signal that represents the viscosity determined by the detection device. The Doppler spectrum is to be understood as a product from a flow profile of the fluid and a directional characteristic of an ultrasonic element, which generates or can generate a sound wave in the fluid. The flow profile can be dependent on a flow velocity of the fluid and additionally or alternatively on a shaping of an intake device through which the fluid flows.

The detection device can be designed to read the Doppler parameter from such an ultrasonic element, which can be an ultrasonic transducer. The ultrasonic element can be formed to generate the sound wave in the fluid and to sense the Doppler parameter of a returning reflected sound wave in the fluid. The generated sound wave can have a defined or fixed directional characteristic. The detection device and/or the provisioning device can be part of, or be formed to be coupled to, the ultrasonic element. For example, the detection device can be formed to read the Doppler parameter sensed by the ultrasonic element from the ultrasonic element.

The detection device can be formed to determine the viscosity using a functional relationship between the Doppler parameter to the viscosity and/or using a lookup table, in particular wherein a relationship between the Doppler parameter to the viscosity can be stored in the lookup table. The look-up table can be a calibration table that can store measurement data for all relevant viscosities of the fluid for all relevant Doppler parameters and additionally or alternatively other relevant parameters such as flow velocities of the fluid. Using the real-time Doppler parameter, a viscosity mapped thereto can then be read quickly and easily from the look-up table. Or the viscosity can be quickly and easily determined by solving the functional relationship using the real-time Doppler parameter. The lookup table and/or the functional relationship can be stored in the detection device or can be read for use by the detection device.

It is also advantageous if the detection device is formed according to an embodiment to determine the viscosity using an interpolation of a first viscosity stored in the lookup table and a second (adjacent) viscosity stored in the lookup table. This allows calculation accuracy to be increased.

The analysis device can also comprise a cannula having an intake interface for receiving the fluid and an outlet interface opposite the intake interface for discharging the fluid, in particular wherein the Doppler parameter can represent a Doppler parameter in the cannula. Such a cannula can be formed for use on or in a cardiac assist system. For example, the cannula can be shaped or formed to receive blood as the fluid. The real-time viscosity of the blood in the cannula can then be advantageously determined using the analysis device. The detection device can also be formed to determine the viscosity using at least one cannula parameter of the cannula. The cannula parameter can be a cannula width or a cannula radius.

According to a further advantageous embodiment, the analysis device comprises a flow device for conveying the fluid from the intake interface to the outlet interface of the cannula, in particular wherein the flow device can be arranged or arrangeable on or in the area of the outlet interface. The flow device can comprise a drive device in the form of an electric motor and a coupled impeller. When the flow device is in operation, a volume flow of the fluid can thus be caused through the cannula, wherein the volume flow renders the flow profile measurable as a function of the viscosity of the fluid, a flow velocity of the fluid, and a shaping of the cannula, for example the cannula width or the cannula radius. Such an analysis device with a flow device can be formed or usable as a cardiac assist system. This cardiac assist system can advantageously determine a real-time blood viscosity and provide or transmit it for example for a diagnostic method.

The detection device can also be formed to determine the viscosity using at least one flow parameter of the flow profile, in particular a flow velocity, of the fluid through the cannula. The flow velocity can be measurable using an ultrasonic element formed to sense the Doppler shift of the ultrasonic signal reflected on particles of the fluid.

It is further advantageous if the analysis device according to an exemplary embodiment comprises an ultrasonic element, which is formed to generate a sound wave in the fluid in order to detect the Doppler parameter, in particular wherein the ultrasonic element can be arranged in the region of the intake interface of the cannula. The ultrasonic element can be formed to generate the sound wave with a defined or fixed directional characteristic. In this case, the directional characteristic can be aligned in the direction of the expected fluid flow of the fluid through the cannula.

The detection device can be formed to determine the viscosity using the Doppler parameter, which represents a Doppler frequency and/or a width of the Doppler spectrum.

A method for analyzing a viscosity of a fluid is also presented. The method comprises a detection step and a provisioning step. The detection step involves determining the viscosity of the fluid using at least one Doppler parameter of a Doppler spectrum of the fluid. The provisioning step involves providing or transmitting a viscosity signal, which represents the viscosity determined during the detection step.

This method can be performed using the analysis device presented above. The method can be implemented in software or hardware, for example, or in a mixed form of software and hardware, for example in a control device.

A computer program product or computer program having program code which can be stored on a machine-readable carrier or storage medium such as a semiconductor memory, a hard drive memory, or optical memory and is used to carry out, implement, and/or control the steps of the method according to one of the embodiments described above is also advantageous, in particular if the program product or program is executed on a computer or a device.

Design examples of the approach presented here are shown in the drawings and explained in more detail in the following description. The drawings show in:

DETAILED DESCRIPTION

The following description of favorable exemplary embodiments of the present invention uses the same or similar reference symbols shown in the various figures for elements that act in similar ways, wherein a repeated description of these elements is omitted.

If a design example includes an "and/or" conjunction between a first feature and a second feature, this should be read to mean that the design example according to one embodiment comprises both the first feature and the second feature and, according to another embodiment, comprises either only the first feature or only the second feature.

Figure 1:
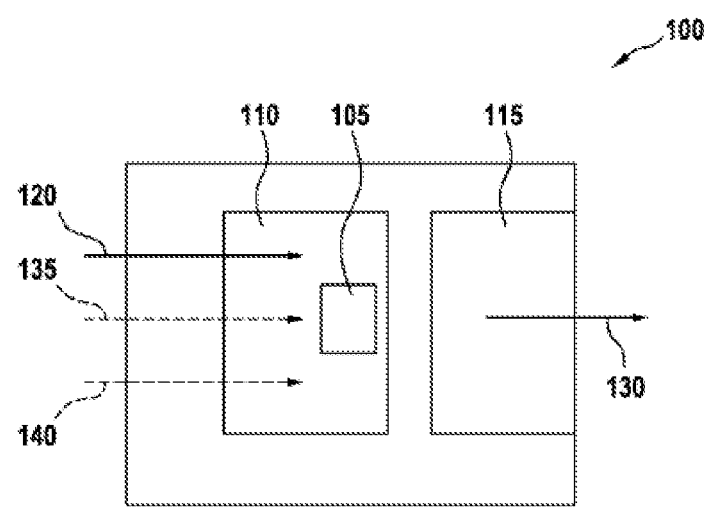
FIG. 1 a schematic illustration of an analysis device for analyzing a viscosity of a fluid according to an exemplary embodiment.

FIG. 1 shows a schematic illustration of an analysis device 100 for analyzing a viscosity 105 of a fluid according to an exemplary embodiment.

The analysis device 100 comprises a detection device 110 and a provisioning device 115. The detection device 110 is formed to detect the viscosity 105 of the fluid using at least one Doppler parameter 120 of a Doppler spectrum of the fluid. The provisioning device 115 is formed to provide or transmit a viscosity signal 130 representing the viscosity 105 determined by the detection device 110.

According to this exemplary embodiment, the detection device 110 is designed to determine the viscosity 105 using a flow parameter 135 of the fluid through a cannula, in which the fluid is accommodated, and/or to determine a cannula parameter 140 of the cannula. According to this exemplary embodiment, the detection device 110 is formed to read the Doppler parameter 120 and/or the flow parameter 135 and/or the cannula parameter 140 in the form of a sensor signal each.

Figure 2:
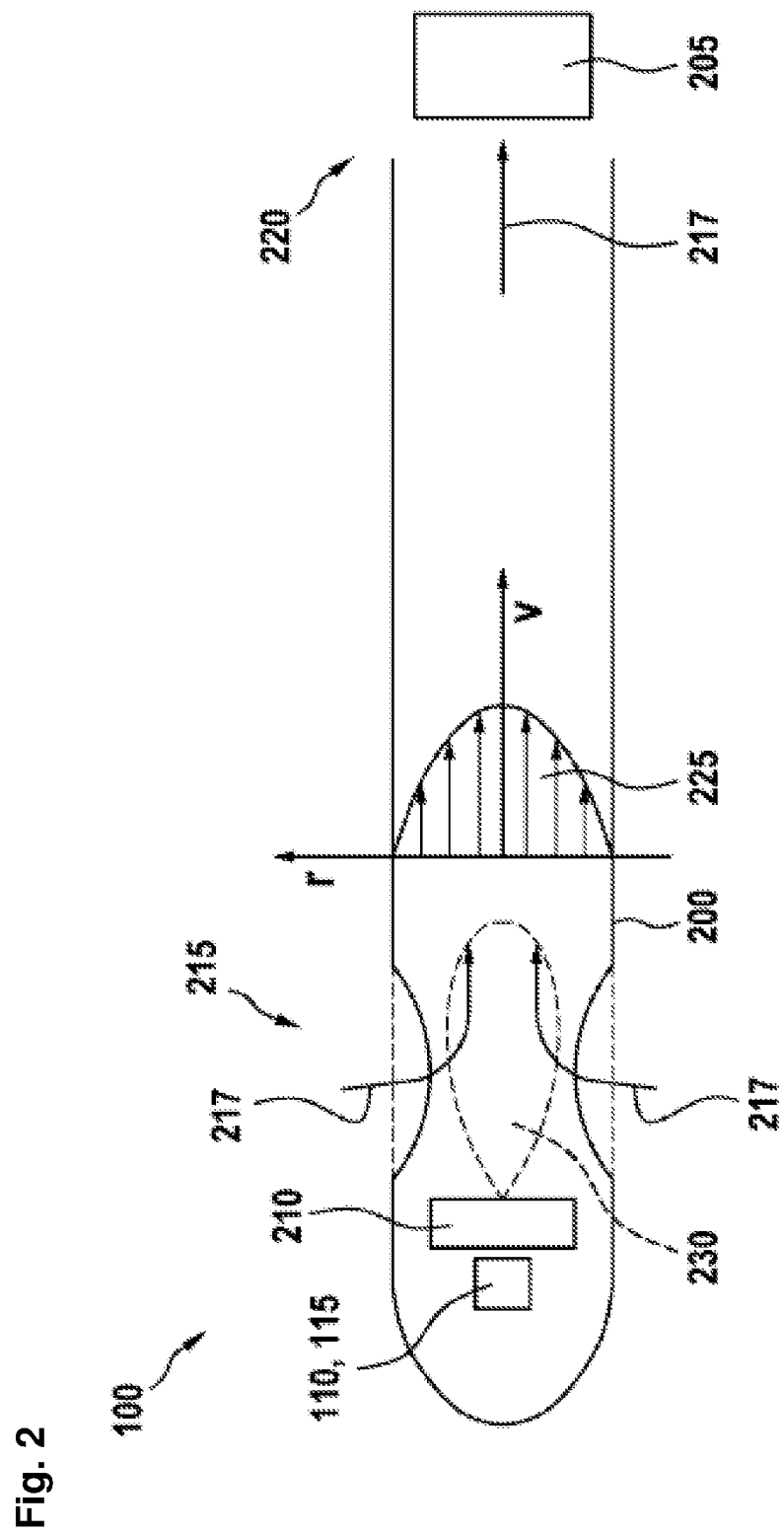
FIG. 2 a schematic cross-sectional side view illustration of an analysis device according to an exemplary embodiment.

FIG. 2 shows a schematic cross-sectional side view of an analysis device 100 according to an exemplary embodiment. This can be the analysis device 100 described in FIG. 1, with the difference being that the analysis device 100 according to this exemplary embodiment additionally comprises a cannula 200, a flow device 205 and an ultrasonic element 210. Alternatively or additionally, the analysis device 100 can for example be formed as two components so that the cannula 200, the flow device 205 and the ultrasonic element 210 can be operated spatially separated from the detection device 110 and the provision device 115 using a cable.

The cannula 200 has an intake interface 215 formed to receive the fluid 217 and an outlet interface 220 formed to discharge the fluid 217 opposite the intake interface 215. According to this exemplary embodiment, the Doppler parameter represents a Doppler parameter in the cannula 200.

The flow device 205 is formed to convey the fluid 217 from the intake interface 215 to the outlet interface 220 of the cannula 200. For this purpose, the flow device 205 according to this exemplary embodiment is arranged or can be arranged on or in the area of the outlet interface 220. According to this exemplary embodiment, the flow device 205 comprises a drive device in the form of an electric motor and/or a coupled impeller, which is accommodated in the cannula 200.

According to this exemplary embodiment, the detection device 110 is formed to determine the viscosity using the flow parameter, which represents a flow velocity v of a flow profile 225 of the fluid through the cannula 200. According to this exemplary embodiment, the detection device 110 is also formed to determine the viscosity using the cannula parameter of the cannula 200, which represents a cannula width r of the cannula 200.

The ultrasonic element 210 is formed to generate a sound wave in the fluid 217 in order to determine the Doppler parameter in the reflection of the sound waves on particles in the fluid.

According to this exemplary embodiment, the ultrasonic element 210 is arranged in the region of the intake interface 215 of the cannula 200. A directional characteristic 230 of the ultrasonic element 210 is also shown, wherein the directional characteristic 230 is fixed and/or defined according to this exemplary embodiment.

According to this exemplary embodiment, the detection device 110 is formed to determine the viscosity using the Doppler parameter, which represents a Doppler frequency and/or a width of the Doppler spectrum. According to this exemplary embodiment, the detection device 110 is formed to determine the viscosity using a functional relationship between the Doppler parameter to the viscosity and/or using a lookup table, wherein a relationship between the Doppler parameter and the viscosity is stored in the lookup table. According to this exemplary embodiment, the detection device 110 is also formed to determine the viscosity by using an interpolation of a first viscosity stored in the lookup table and an adjacent second viscosity stored in the lookup table.

The following again describes details of the analysis device 100 in more detail and in other words:

According to this exemplary embodiment, the analysis device 100 presented here can be used as a cardiac assist system. For patients with a cardiac assist system, also called VAD patients, where VAD stands for "Ventricular Assist Device", coagulation management is essential to minimize pump thrombosis. For this purpose, patients are for example treated with drugs for inhibiting plasma blood coagulation, and the INR is thus for example adjusted in the range 2 to 2.5.

The flow profile 225 and thus the viscosity of the blood can be determined by analyzing the Doppler spectrum with the ultrasonic element 210 integrated according to this exemplary embodiment in a tip of the cannula 200 of a VAD system, which can also be referred to as an inlet cannula.

In accordance with this exemplary embodiment, the blood viscosity is determined by the detection device 110 while the analysis device 100 is in operation, either continuously or at fixed time intervals in accordance with an alternative exemplary embodiment. The provisioning device 115 is formed to provide a physician and/or patient with the determined viscosity as a parameter for therapy management. For this purpose, the viscosity signal is formed to display the viscosity on a display and/or to transmit it to a web service by wireless transmission.

Advantageously, in the analysis device 100 presented here, only a simple so-called "single element" ultrasonic transducer is sufficient as an ultrasonic element 210, which is formed according to this exemplary embodiment as a circular disk. Such an ultrasonic element 210 is possible due to the special spatial positioning of the ultrasonic element 210 shown here in the direction of the expected flow of the fluid 217. The ultrasonic element 210 is formed according to an exemplary embodiment for quantifying the flow velocity v of the fluid 217.

The ultrasonic element 210 integrated in the tip of the intake cannula measures the Doppler spectrum of the flow in the cannula 200, for example with the so-called "pulsed-wave Doppler" method; this method is also called a "pulsed Doppler".

In other words, FIG. 2 shows an exemplary embodiment of a VAD intake cannula with ultrasonic element 210 in the form of an ultrasonic transducer. FIG. 2 shows an intake region, the directional characteristic 230 of the ultrasonic transducer, and the adjusting flow profile 225 in the intake cannula.

Figure 3:
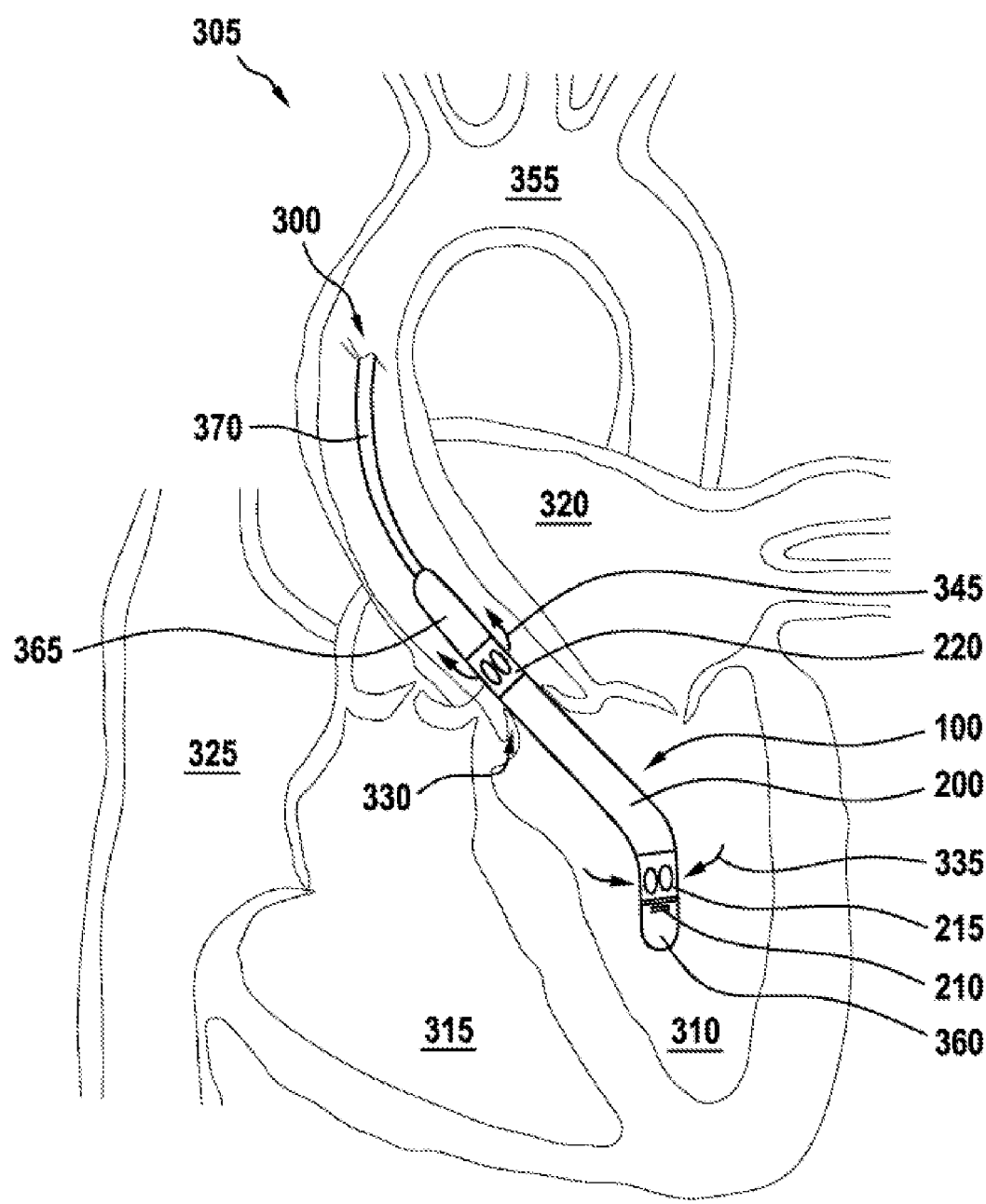
FIG. 3 a schematic illustration of a cardiac assist system with an analysis device according to an exemplary embodiment.

FIG. 3 shows a schematic illustration of a cardiac assist system 300 with an analysis device 100 according to an exemplary embodiment. This can be the analysis device 100 described with reference to FIG. 2.

The cardiac assist system 300 shown here as an example can also be referred to as a cardiac assist system. FIG. 3 also shows a heart 305 with left ventricle 310 and right ventricle 315 as well as left atrium 320 and right atrium 325. The cardiac assist system 300 is located in the center of the aortic valves 330, so that a blood stream 335 is suctioned through the intake interface 215 in the form of intake openings in the region of the left ventricle 310, and is discharged into the aorta 355 in the region downstream of the heart valves 345 through the outlet interface 220 in the form of outlet openings.

According to this exemplary embodiment, the assist system also comprises a distal tip 360 with sensors; according to an exemplary embodiment, the sensors comprise at least one pressure and/or at least one temperature sensor, as well as the ultrasonic element 210, which radiates into the cannula 200 along the axis of the support system through an intake region of the intake interface 215. The cannula 200 directs the blood to the flow machine with impeller, which is located in the area of the outlet interface 220. This is followed by an electric motor 365 and a connection cable 370.

Figure 4:
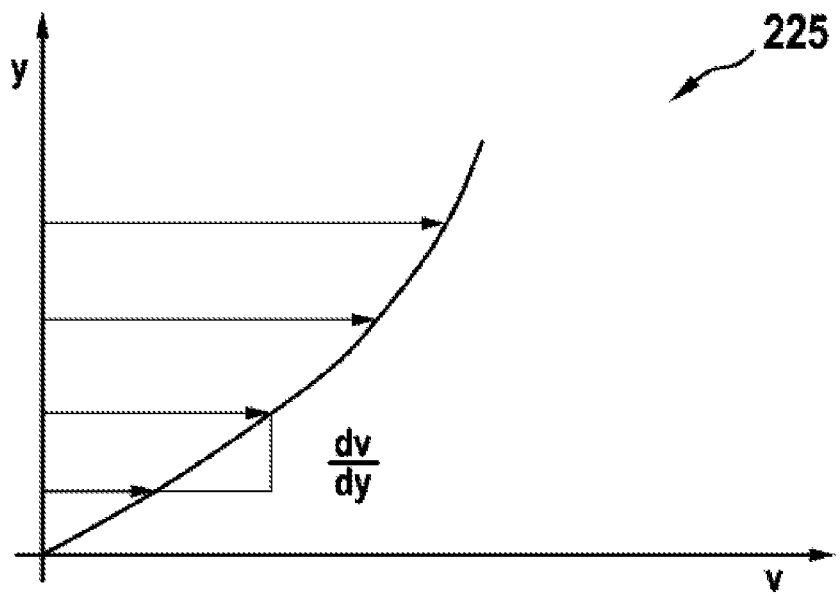
FIG. 4 a schematic illustration of a flow profile of a fluid according to an exemplary embodiment.

FIG. 4 shows a schematic illustration of a flow profile 225 of a fluid according to an exemplary embodiment. This can be the flow profile 225 described in FIG. 2, which can be determined by one of the analysis devices described in one of the preceding figures. An exemplary flow profile 400 is shown in a tube, wherein v denotes a velocity of the fluid and y a radial distance from a tube inner wall of the tube. The velocity gradient $\partial v/\partial y$, and thus the velocity profile, is viscosity-dependent. In other words, the velocity profile in a cannula of a cardiac assist system according to Navier-Stokes is dependent on the viscosity.

Figure 5:
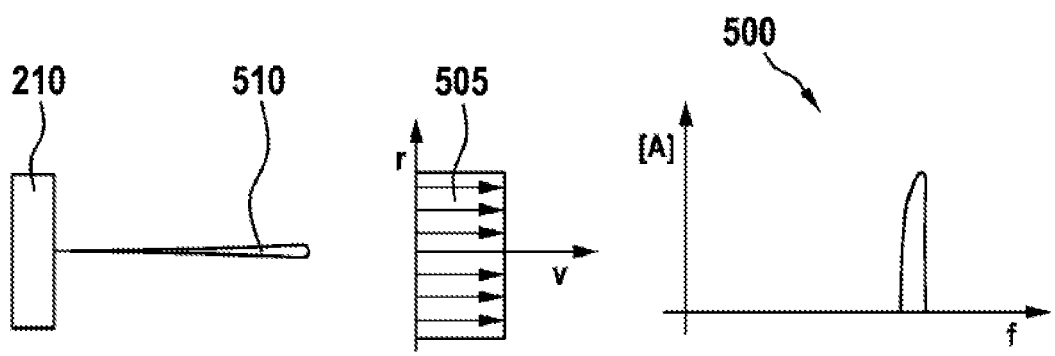
FIG. 5 a schematic illustration of a Doppler spectrum.
Figure 6:
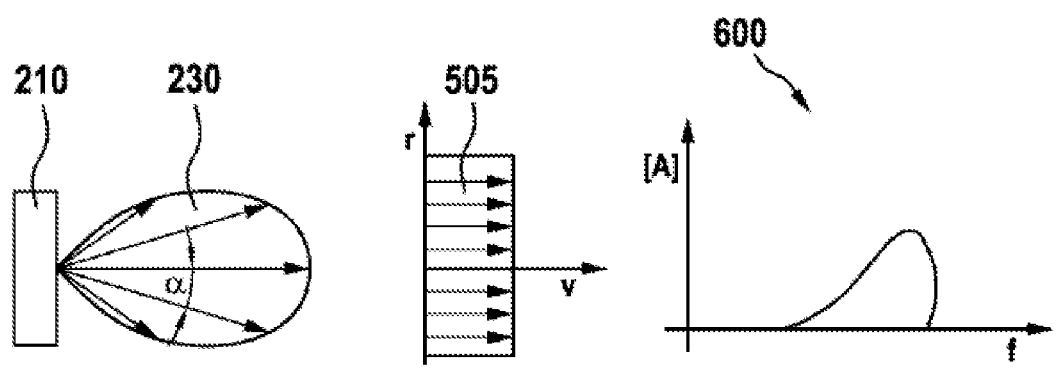
FIG. 6 a schematic illustration of a Doppler spectrum.
Figure 7:
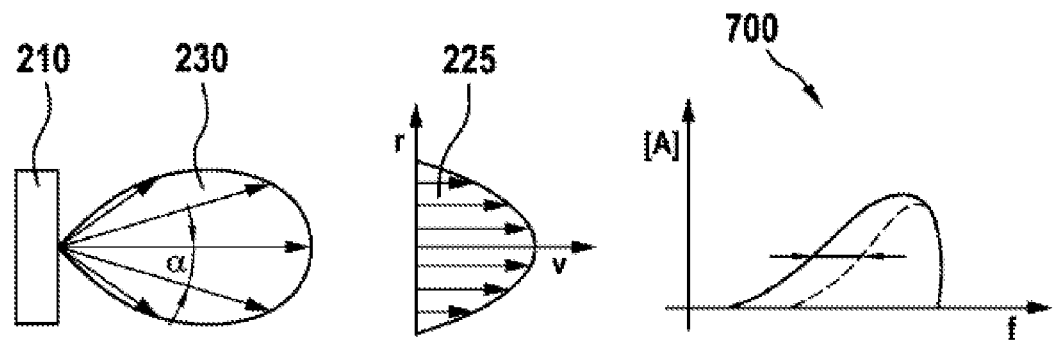
FIG. 7 a schematic illustration of a Doppler spectrum according to an exemplary embodiment.

FIG. 5 shows a schematic illustration of a Doppler spectrum 500. The Doppler spectrum 500 is the product of a flow profile 505 of a fluid and a directional characteristic 510 of an ultrasonic element 210. FIGS. 5 to 7 compare different flow profiles and directional characteristics as well as respectively resulting Doppler spectra, wherein FIG. 7 shows a real Doppler spectrum in the manner effected and/or discernable using the analysis devices presented in any of FIGS. 1 to 3.

FIG. 5 shows a Doppler spectrum 500 for an ideally focusing ultrasonic element 210, which causes an ideal directional characteristic 510, and a parallel flow, which results in the parallel flow profile 505.

FIG. 6 shows a schematic illustration of a Doppler spectrum 600. The figure shows a resulting Doppler spectrum 600 for a real focusing ultrasonic element 210, which causes the directional characteristic 230 described for use with the analytical device described in any of FIGS. 1 to 3, and the parallel flow profile 505 described in FIG. 5. Compared to the Doppler spectrum shown in FIG. 5, the Doppler spectrum 600 resulting in FIG. 6 is widened.

FIG. 7 shows a schematic illustration of a Doppler spectrum 700 according to an exemplary embodiment. This can be the Doppler spectrum 700, as is caused and/or discernible in the cannula using the analysis devices shown in any of FIGS. 1 to 3.

The figure shows a resulting Doppler spectrum 700 of the fluid for the real focusing ultrasonic element 210, which has a real directional characteristic 230, and a real flow profile 225 as generated in the cannula.

Higher viscosities cause a further widening of the Doppler spectrum 700 because the flow flows faster in the middle and slower at the perimeter for a given volume flow of the fluid, and the areas of slow flow take up more cross-sectional area in the focus area of the ultrasonic element 210.

The Doppler frequency shifts of all velocities V, occurring in the flow profile 225 and shown in the Doppler spectrum are:

$$\Delta f_i = f_0 \frac{2v_i}{c} \cos(\alpha_i)$$

The peak in the Doppler spectrum 700 represents the dominant velocity, or the most frequently occurring velocity analogous to a histogram. However, this value is still biased with the directional characteristic 230 of the ultrasonic element 210, which does not operate with equal sensitively in all directions.

The most frequently occurring Doppler frequency represents the most frequently occurring velocity, since the latter is to be expected due to the special mechanical design in the main direction of radiation of the ultrasonic element 210, because:

$$\alpha_{0°} = \rightarrow 0 \quad \cos(\alpha_{0°}) = 1.$$

For a given ultrasonic element 210 with a fixed directional characteristic 230, a width of the Doppler spectrum 700 correlates with a velocity distribution in the observation space. The detection device relies on characteristic figures of the Doppler spectrum 700 as a calculation metric—according to an exemplary embodiment based on the parameters Doppler frequency at half the maximum amplitude of the Doppler spectrum 700 and/or width of the Doppler spectrum 700, according to an exemplary embodiment at an exemplary 90% of the peak value and/or frequency of the maximum amplitude of the Doppler spectrum 700 and maximum Doppler frequency in the Doppler spectrum 700.

The calculation or the determination of the viscosity are carried out according to an exemplary embodiment by the detection device in a calculation-efficient manner using a lookup table or calibration table, abbreviated as LUT, which stores measurement data for all relevant viscosities at all relevant flow velocities. Based on the dominant Doppler frequency, a column for the dominant flow velocity is selected according to an exemplary embodiment and the viscosity is read from said column according to an exemplary embodiment based on the width of the Doppler spectrum 700. According to an exemplary embodiment, the calculation accuracy is further increased by interpolating between adjacent table entries.

A use of the flow profile 225 of the analysis device presented here for viscosity determination is demonstrated by experimentally generating different flow profiles. In an exemplary embodiment with an ultrasonic element 210, the ultrasonic element 210 is visually detectable.

Figure 8:
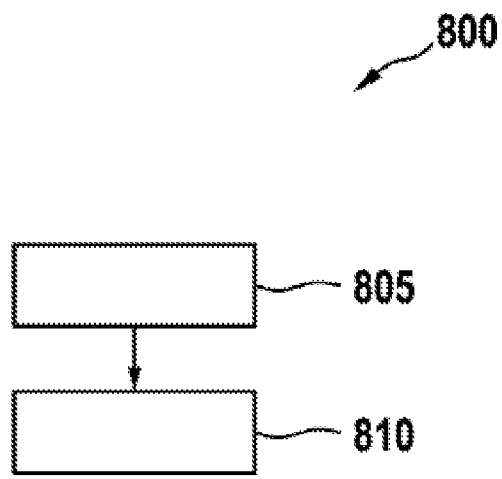
FIG. 8 a flow diagram of a method for analyzing a viscosity of a fluid according to an exemplary embodiment.

FIG. 8 shows a flow chart of a method 800 for analyzing a viscosity of a fluid according to an exemplary embodiment. This can be a method 800 that is executable by any of the analysis devices described in the figures above.

The method 800 includes detection as a step 805 and provisioning as a step 810. The detection step 805 involves determining the viscosity of the fluid using at least one Doppler parameter of a Doppler spectrum of the fluid. The provisioning step 810 involves providing or transmitting a viscosity signal that represents the viscosity determined during the detection step 805.

The method steps 805, 810 presented here can be repeated and carried out in a sequence other than that described.

The invention claimed is:

1. A cardiac assist system comprising:
   an inlet interface having inlet openings;
   an outlet interface having outlet openings;
   a flow machine comprising:
   an impeller coupled to an electric motor;
   a connection cable; and
   a cannula through which a blood flow can be conveyed by the flow machine from the inlet interface to the outlet interface, the cannula configured to extend along an axis across a patient's aortic valve and be coupled to the connection cable, wherein a tip of the cannula is located at a distal end of the cannula; and
   an analysis device configured to analyze a viscosity of blood in a blood flow of the patient, the analysis device comprising:
   an ultrasonic element arranged in the tip and configured to generate a sound wave in the blood, wherein the sound wave radiates through the inlet interface into the cannula along the axis and reflects off the blood,
   a detection device configured to determine the viscosity of the blood using at least one Doppler parameter of a Doppler spectrum of the sound wave reflected off the blood, wherein the detection device is configured to determine the viscosity using a functional relationship between the Doppler Parameter and the viscosity; and
   a provisioning device configured to provide a viscosity signal representing the viscosity of the blood that is detected by the detection device.

2. The cardiac assist system of claim 1, wherein the detection device is configured to determine the viscosity using a lookup table.

3. The cardiac assist system of claim 2, wherein the lookup table comprises values characterizing a relationship between the Doppler parameter and the viscosity.

4. The cardiac assist system of claim 2, wherein the lookup table comprises an interpolation of a first viscosity and a second viscosity and wherein the detection device is configured to determine the viscosity using the interpolation of the first viscosity and the second viscosity.

5. The cardiac assist system of claim 1, wherein the detection device is configured to determine the viscosity using at least one cannula parameter (r) of the cannula.

6. The cardiac assist system of claim 1, wherein the flow device is arranged at the outlet interface.

7. The cardiac assist system of claim 1, wherein the detection device is configured to determine the viscosity using at least one flow parameter of a flow profile.

8. The cardiac assist system of claim 7, wherein the at least one flow parameter comprises a flow velocity (v) of the fluid through the cannula.

9. The cardiac assist system of claim 1, wherein the detection device is configured to determine the viscosity using the Doppler parameter and wherein the Doppler parameter comprises a Doppler frequency or a width of the Doppler spectrum.

10. A method for analyzing a viscosity of blood in a bloodstream of a patient conveyed by a flow device through a cannula which is extended along an axis, the method comprising:
generating a sound wave in the blood by an ultrasonic element, wherein the sound wave radiates through an inlet area of an inlet interface of the cannula and into the cannula along its axis and reflects off the blood; and
determining the viscosity of the blood in the bloodstream using at least one Doppler parameter of a Doppler spectrum, wherein determining the viscosity comprises applying a functional relationship between the Doppler parameter and the viscosity.

11. The method of claim 10, wherein determining the viscosity comprises using a lookup table to determine the viscosity based on the Doppler parameter.

12. The method of claim 11, wherein the lookup table comprises values characterizing a relationship between the Doppler parameter and the viscosity.

13. The method of claim 11, wherein the lookup table comprises an interpolation of a first viscosity and a second viscosity and wherein the detection device is configured to determine the viscosity using the interpolation of the first viscosity and the second viscosity.

14. The method of claim 10, wherein determining the viscosity comprises using at least one cannula parameter (r) of the cannula.

15. The method of claim 10, wherein determining the viscosity comprises using at least one flow parameter of a flow profile.

16. The method of claim 15, wherein the at least one flow parameter comprises a flow velocity (v) of the fluid through the cannula.

17. The method of claim 10, wherein the at least one Doppler parameter comprises a Doppler frequency or a width of the Doppler spectrum.

18. A cardiac assist system comprising:
an inlet interface having inlet openings;
an outlet interface having outlet openings;
a flow machine comprising:
  an impeller coupled to an electric motor;
  a connection cable; and
  a cannula through which a blood flow can be conveyed by the flow machine from the inlet interface to the outlet interface, the cannula configured to extend along an axis across a patient's aortic valve and be coupled to the connection cable, wherein a tip of the cannula is located at a distal end of the cannula; and
an analysis device configured to analyze a viscosity of blood in a blood flow of the patient, the analysis device comprising:
  an ultrasonic element arranged in the tip and configured to generate a sound wave in the blood, wherein the sound wave radiates through the inlet interface into the cannula along the axis and reflects off the blood,
  a detection device configured to determine the viscosity of the blood using at least one Doppler parameter of a Doppler spectrum of the sound wave reflected off the blood, wherein the detection device is configured to determine the viscosity using a lookup table; and
  a provisioning device configured to provide a viscosity signal representing the viscosity of the blood that is detected by the detection device.

19. The cardiac assist system of claim 18, wherein the lookup table comprises values characterizing a relationship between the Doppler parameter and the viscosity.

20. The cardiac assist system of claim 18, wherein the lookup table comprises an interpolation of a first viscosity and a second viscosity and wherein the detection device is configured to determine the viscosity using the interpolation of the first viscosity and the second viscosity.

21. A cardiac assist system comprising:
an inlet interface having inlet openings;
an outlet interface having outlet openings;
a flow machine comprising:
  an impeller coupled to an electric motor;
  a connection cable; and
  a cannula through which a blood flow can be conveyed by the flow machine from the inlet interface to the outlet interface, the cannula configured to extend along an axis across a patient's aortic valve and be coupled to the connection cable, wherein a tip of the cannula is located at a distal end of the cannula; and
an analysis device configured to analyze a viscosity of blood in a blood flow of the patient, the analysis device comprising:
  an ultrasonic element arranged in the tip and configured to generate a sound wave in the blood, wherein the sound wave radiates through the inlet interface into the cannula along the axis and reflects off the blood,
  a detection device configured to determine the viscosity of the blood using at least one Doppler parameter of a Doppler spectrum of the sound wave reflected off the blood, wherein the detection device is configured to determine the viscosity using at least one cannula parameter (r) of the cannula; and
  a provisioning device configured to provide a viscosity signal representing the viscosity of the blood that is detected by the detection device.

22. A cardiac assist system comprising:
an inlet interface having inlet openings;
an outlet interface having outlet openings;
a flow machine comprising:
  an impeller coupled to an electric motor;
  a connection cable; and
  a cannula through which a blood flow can be conveyed by the flow machine from the inlet interface to the outlet interface, the cannula configured to extend along an axis across a patient's aortic valve and be coupled to the connection cable, wherein a tip of the cannula is located at a distal end of the cannula; and
an analysis device configured to analyze a viscosity of blood in a blood flow of the patient, the analysis device comprising:
  an ultrasonic element arranged in the tip and configured to generate a sound wave in the blood, wherein the sound wave radiates through the inlet interface into the cannula along the axis and reflects off the blood,
  a detection device configured to determine the viscosity of the blood using at least one Doppler parameter of a Doppler spectrum of the sound wave reflected off the blood, wherein the detection device is configured to determine the viscosity using the Doppler parameter and wherein the Doppler parameter comprises a Doppler frequency or a width of the Doppler spectrum; and a provisioning device configured to provide a viscosity signal representing the viscosity of the blood that is detected by the detection device.

23. A method for analyzing a viscosity of blood in a bloodstream of a patient conveyed by a flow device through a cannula which is extended along an axis, the method comprising:

generating a sound wave in the blood by an ultrasonic element, wherein the sound wave radiates through an inlet area of an inlet interface of the cannula and into the cannula along its axis and reflects off the blood; and determining the viscosity of the blood in the bloodstream using at least one Doppler parameter of a Doppler spectrum, wherein determining the viscosity comprises using a lookup table to determine the viscosity based on the Doppler parameter.

24. The method of claim 21, wherein the lookup table comprises values characterizing a relationship between the Doppler parameter and the viscosity.

25. The method of claim 21, wherein the lookup table comprises an interpolation of a first viscosity and a second viscosity and wherein the detection device is configured to determine the viscosity using the interpolation of the first viscosity and the second viscosity.

26. A method for analyzing a viscosity of blood in a bloodstream of a patient conveyed by a flow device through a cannula which is extended along an axis, the method comprising:

generating a sound wave in the blood by an ultrasonic element, wherein the sound wave radiates through an inlet area of an inlet interface of the cannula and into the cannula along its axis and reflects off the blood; and determining the viscosity of the blood in the bloodstream using at least one Doppler parameter of a Doppler spectrum, wherein the at least one Doppler parameter comprises a Doppler frequency or a width of the Doppler spectrum.

* * * * *